United States Patent
Wheatley et al.

(10) Patent No.: US 9,295,384 B2
(45) Date of Patent: Mar. 29, 2016

(54) IMAGING PROBES AND ASSOCIATED DEVICES, SYSTEMS, AND METHODS UTILIZING LEVER ARM ACTUATORS

(71) Applicant: NOVARTIS AG, Basel (CH)

(72) Inventors: Barry L. Wheatley, Oceanside, CA (US); Kambiz Parto, Laguna Hills, CA (US)

(73) Assignee: Novartis AG (CH)

( * ) Notice: Subject to any disclaimer, the term of this patent is extended or adjusted under 35 U.S.C. 154(b) by 140 days.

(21) Appl. No.: 14/280,116

(22) Filed: May 16, 2014

(65) Prior Publication Data
US 2015/0327759 A1 Nov. 19, 2015

(51) Int. Cl.
*A61B 5/00* (2006.01)
*A61B 3/10* (2006.01)
*A61B 3/00* (2006.01)
*A61B 3/14* (2006.01)
*G02B 3/00* (2006.01)

(52) U.S. Cl.
CPC .............. *A61B 3/102* (2013.01); *A61B 3/0025* (2013.01); *A61B 3/10* (2013.01); *A61B 3/14* (2013.01); *G02B 3/0087* (2013.01)

(58) Field of Classification Search
CPC .......... A61B 3/102; A61B 18/20; A61B 1/07; A61B 2018/209

USPC .................................................. 600/478, 476
See application file for complete search history.

(56) References Cited

U.S. PATENT DOCUMENTS

| | | | |
|---|---|---|---|
| 6,485,413 B1 | 11/2002 | Boppart et al. | |
| 8,655,431 B2 * | 2/2014 | Joos ....................... | A61B 18/20 600/108 |
| 2010/0228238 A1 | 9/2010 | Brennan et al. | |
| 2013/0207328 A1 | 8/2013 | Awtar et al. | |

* cited by examiner

*Primary Examiner* — Hung Dang

(57) ABSTRACT

Devices, systems, and methods that utilize a mechanical structure, such as a lever arm or a flexure mechanism, and an electrically energizable member, such as an actuator, to impart motion to an optical fiber positioned within an imaging probe are provided. In some embodiments, an ophthalmic imaging probe can include a handle; a cannula coupled to the handle; an optical fiber positioned at least partially within the handle and the cannula, the optical fiber configured to receive an imaging light from an imaging light source and guide the imaging light to an optical element positioned within a distal portion of the cannula; and an actuator system configured to impart motion to the optical fiber, the actuator system including a mechanical structure and an electrically energizable member configured to selectively impart motion to the mechanical structure upon the electrically energizable member being electrically energized.

26 Claims, 6 Drawing Sheets

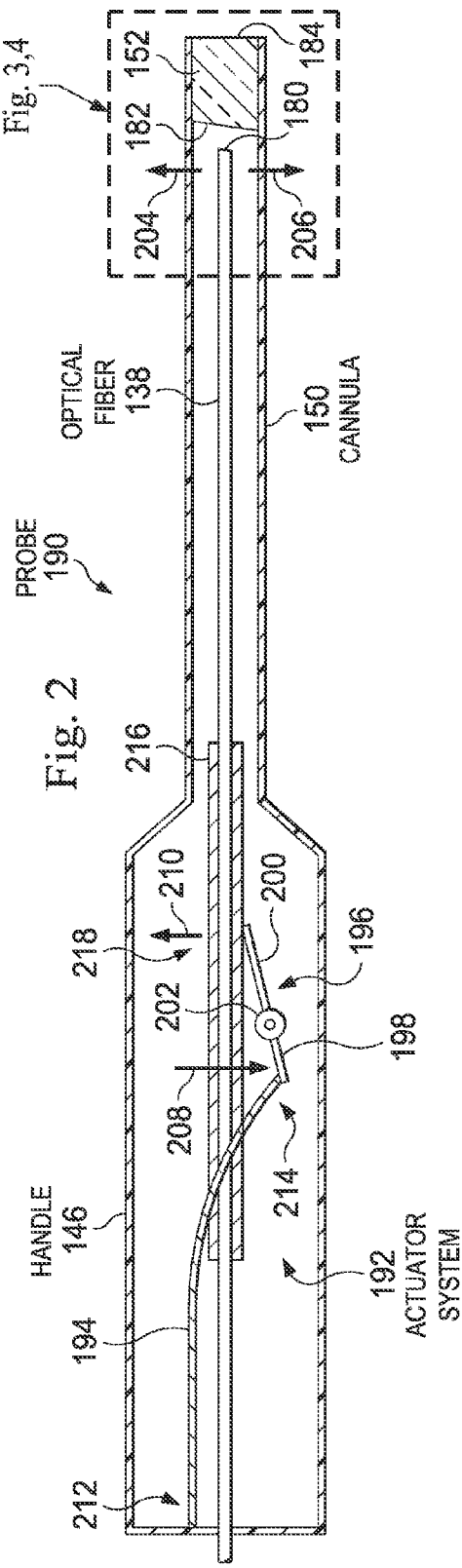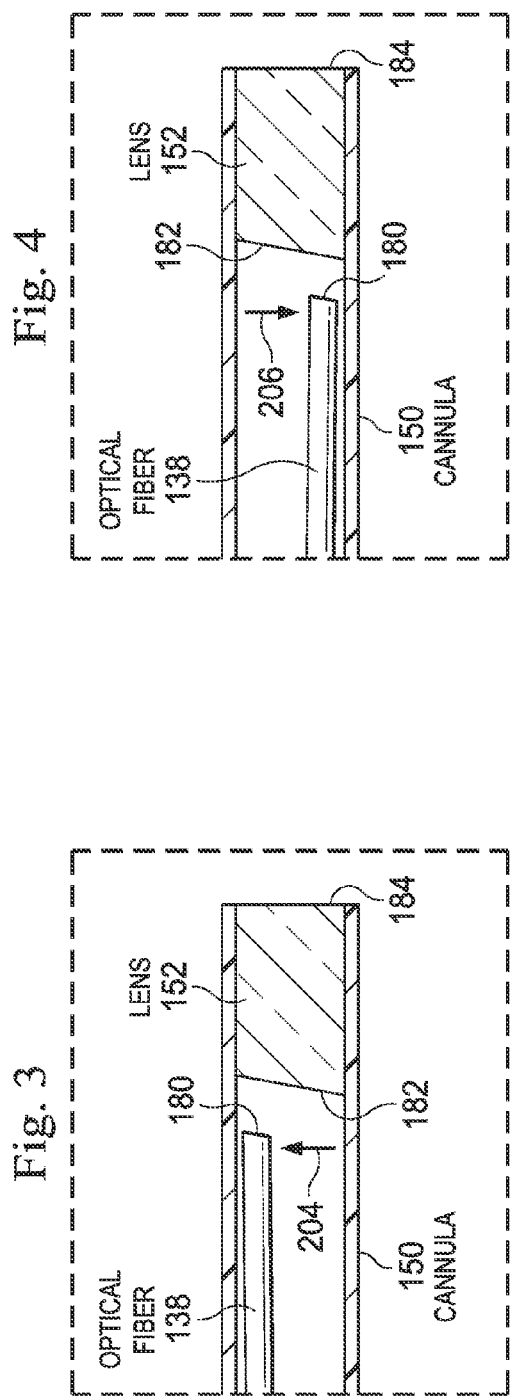

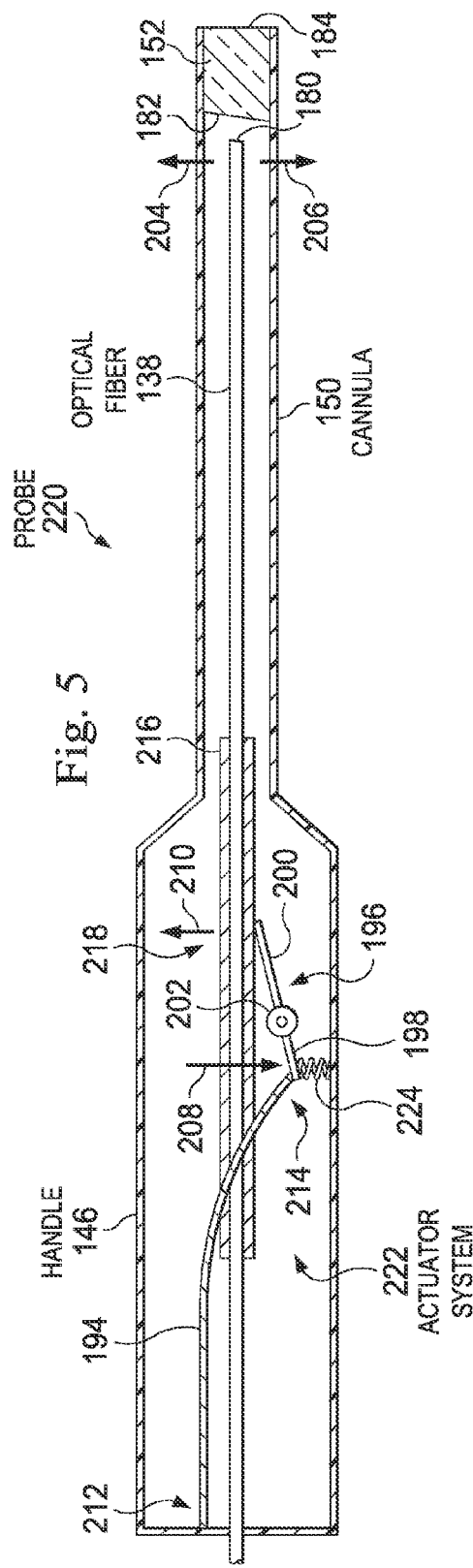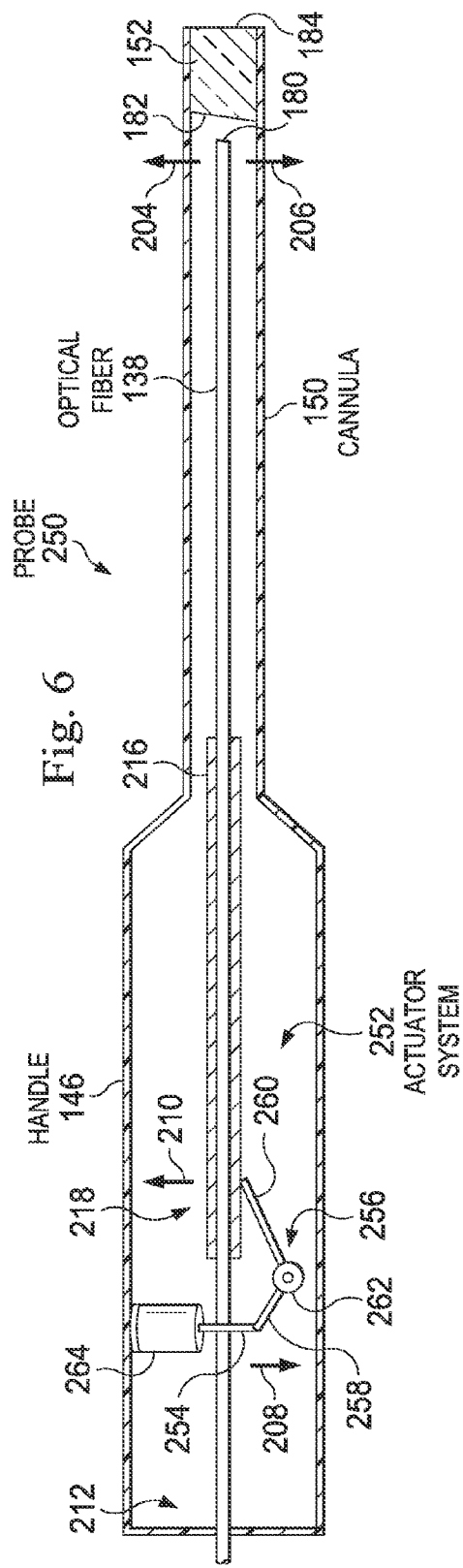

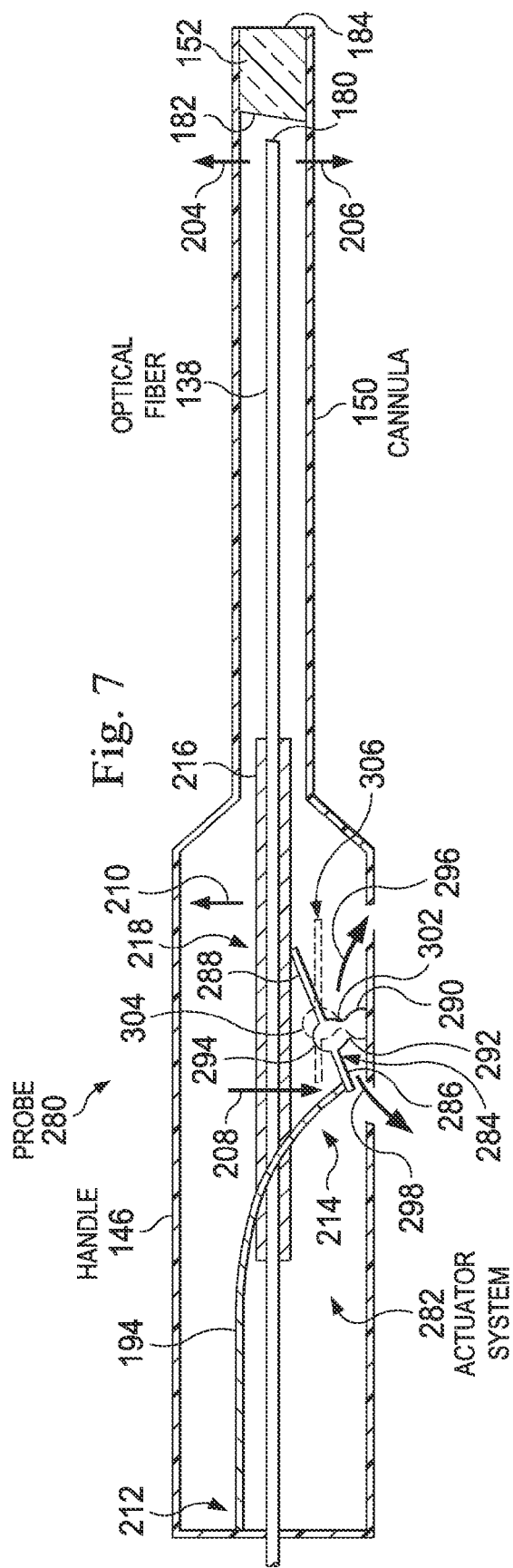

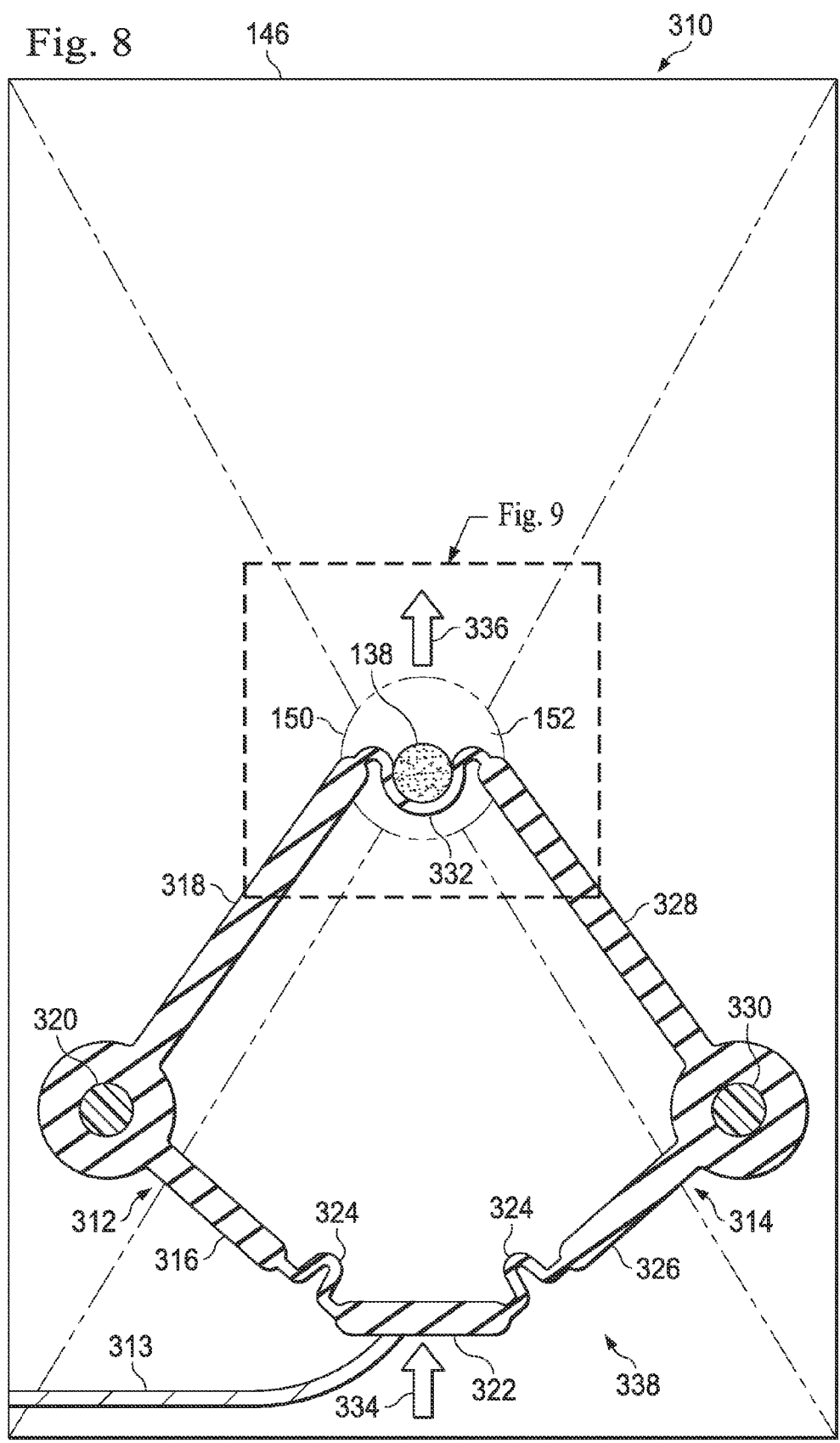

IMAGING PROBES AND ASSOCIATED DEVICES, SYSTEMS, AND METHODS UTILIZING LEVER ARM ACTUATORS

TECHNICAL FIELD

Embodiments disclosed herein are related to devices, systems, and methods for scanning tissue with an optical coherence tomography (OCT) probe, and more particularly, to devices, systems, and methods that utilize an OCT probe having a displaceable fiber for ophthalmic imaging.

BACKGROUND

Optical Coherence Tomography (OCT) systems are used to capture and generate images of patient tissue layers. These systems often include OCT probes that can invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from subsurface features of the tissue and is collected through the same probe. Most of the light is not reflected but, rather, diffusely scatters at large angles. In conventional imaging, this diffusely scattered light contributes background noise that obscures an image. However, in OCT, a technique called interferometry records the optical path lengths of received photons, and provides data that rejects most of the photons that scatter multiple times before detection. This results in images that are clearer and that extend in the depth of the tissue.

The OCT probes often include a projecting cannula that can invasively penetrate patient tissue. The probe scans tissue by refracting the optical light beam through a lens disposed at an end of the cannula. A scan can include moving an optical fiber back and forth within the cannula to direct the light beam through the lens and at the tissue at different angles. The length and small diameter of the cannula make it difficult to move the fiber back and forth within the cannula. Further, the small amount of available space within the probe limits the types of actuators that can be utilized. Further still, the OCT probes and associated systems must be capable of being manufactured in a cost-effective manner, which includes the ability to make the probe as a disposable, one-time use device in some implementations.

SUMMARY

Embodiments disclosed herein are related to devices, systems, and methods that utilize a mechanical structure, such as a lever arm or a flexure mechanism, and an electrically energizable member, such as an actuator, to impart motion to an optical fiber positioned within an imaging probe.

Consistent with some embodiments, an ophthalmic imaging probe is provided. The probe can include a handle; a cannula coupled to the handle; an optical fiber positioned at least partially within the handle and the cannula, the optical fiber configured to receive an imaging light from an imaging light source and guide the imaging light to an optical element positioned within a distal portion of the cannula; and an actuator system configured to impart motion to the optical fiber, the actuator system including a mechanical structure and an electrically energizable member configured to selectively impart motion to the mechanical structure upon the electrically energizable member being electrically energized.

The mechanical structure can be a lever arm. The actuator system can be configured to impart amplified motion to a distal section of the optical fiber. The optical fiber can be coupled to the lever arm so that a distal end of the optical fiber extends past a distal end of the lever arm such that motion imparted to the distal end of the optical fiber is amplified relative to the movement of the lever arm. At least a portion of lever arm can be configured to move relative to the handle in response to the electrically energizable member being electrically energized. The lever arm can be pivotally affixed to the handle by a pivot pin. The lever arm can be movably affixed to the handle by a flexure bearing. The lever arm can include a first section configured to contact the electrically energizable member; and a second section configured to contact with the optical fiber. The actuator system can further include a restoring element configured to counteract the motion imparted to the optical fiber by the lever arm in response to the electrically energizable member being electrically energized. The restoring element can be a flexible restoring element. The electrically energizable member can be configured to impart motion to a first arm of the lever arm in a first direction; and in response to the motion imparted to the first arm of the lever arm by the electrically energizable member, a second arm of the lever arm is moved in a second direction to impart motion to the optical fiber. The second direction can be opposite the first direction. The second direction can be perpendicular to the first direction. A proximal section of the electrically energizable member can be fixedly secured to a proximal portion of the handle. The optical element can include a gradient index (GRIN) lens. The optical element can be mechanically coupled to a distal end of the optical fiber so that the optical element moves with the distal end of the optical fiber. The actuation system can be configured to impart motion to the optical fiber to scan the imaging light along a scanning pattern with a linear extent at a target biological tissue between 1 mm and 5 mm at a distance between 5 mm and 10 mm from a distal end of the handle. A stiffening member can be disposed adjacent to the optical fiber.

The mechanical structure can be a flexure mechanism. The flexure mechanism can include a first vertex configured to be displaced by the electrically energizable member and a second vertex configured to impart motion to the optical fiber in response to displacement of the first vertex. The flexure mechanism can further include a third vertex positioned opposite the first vertex and a fourth vertex positioned opposite the second vertex, the third vertex and fourth vertex are fixedly secured to the handle.

Consistent with some embodiments, an ophthalmic imaging system is provided. The system can include an imaging light source configured to generate an imaging light; an optical guide in optical communication with the imaging light source, the optical guide configured to receive the generated imaging light from the imaging light source; and a probe in optical communication with the optical guide, the probe including a handle; a cannula coupled to the handle; an optical fiber positioned at least partially within the handle and the cannula, the optical fiber configured to receive an imaging light from an imaging light source and guide the imaging light to an optical element positioned within a distal portion of the cannula; and an actuator system configured to impart motion to the optical fiber, the actuator system including a mechanical structure and an electrically energizable member configured to selectively impart motion to the mechanical structure upon the electrically energizable member being electrically energized, wherein the mechanical structure includes at least one of a lever arm and a flexure mechanism.

The system can further include a controller in communication with the light source, the controller configured to control actuation of the imaging light source for an optical coherence tomography (OCT) imaging procedure. The controller can be further configured to process data obtained by the probe and output imaging data to a display in communication with the controller.

Consistent with some embodiments, a method of ophthalmic imaging is provided. The method can include energizing an electrically energizable member positioned within a housing of ophthalmic probe to deflect a lever arm within the housing; wherein deflection of the lever arm causes an optical fiber coupled to the lever arm to scan an imaging light passing through the optical fiber across an optical element positioned within a distal portion of the housing.

Additional aspects, features, and advantages of the present disclosure will become apparent from the following detailed description.

BRIEF DESCRIPTION OF THE DRAWINGS

FIG. 2 is a stylized illustration of a cross-sectional side view of an imaging probe in accordance with an aspect of the present disclosure.

FIG. 3 is a stylized illustration of a cross-sectional side view of a distal portion of the imaging probe of FIG. 2 showing an optical fiber of the imaging probe in a first position in accordance with an aspect of the present disclosure.

FIG. 4 is a stylized illustration of a cross-sectional side view of the distal portion of the imaging probe of FIG. 2, similar to that of FIG. 3, but showing the optical fiber in a second position in accordance with an aspect of the present disclosure.

FIG. 5 is a stylized illustration of a cross-sectional side view of an imaging probe in accordance with another aspect of the present disclosure.

FIG. 6 is a stylized illustration of a cross-sectional side view of an imaging probe in accordance with another aspect of the present disclosure.

FIG. 7 is a stylized illustration of a cross-sectional side view of an imaging probe in accordance with another aspect of the present disclosure.

FIG. 8 is a stylized illustration of a cross-sectional back view of an imaging probe in accordance with another aspect of the present disclosure.

Figure 1:
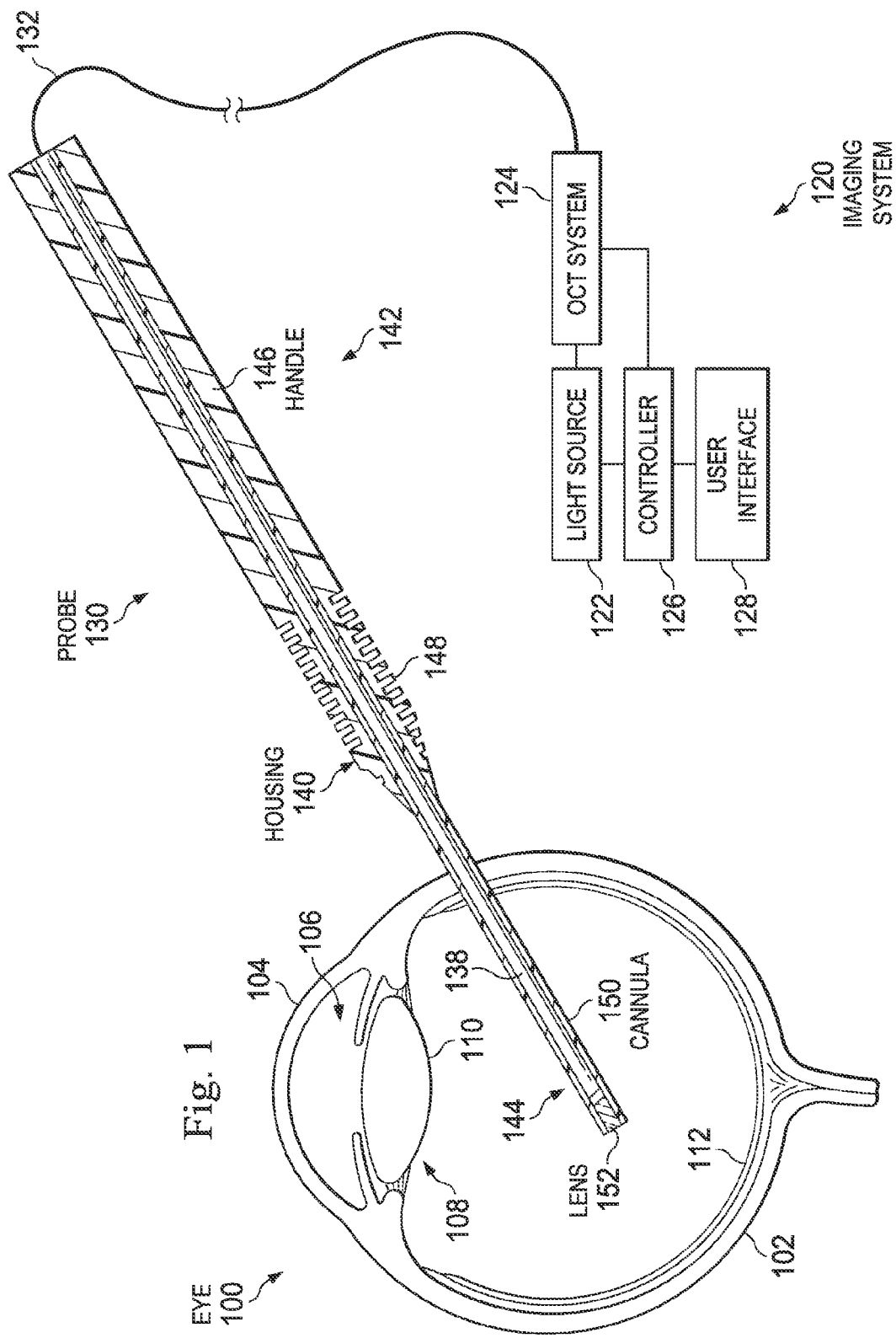
FIG. 1 is a diagrammatic schematic view of an eye under treatment and an exemplary OCT imaging system in accordance with an aspect of the present disclosure.

In the drawings, elements having the same designation have the same or similar functions.

DETAILED DESCRIPTION

In the following description specific details are set forth describing certain embodiments. It will be apparent, however, to one skilled in the art that the disclosed embodiments can be practiced without some or all of these specific details. The specific embodiments presented are meant to be illustrative, but not limiting. One skilled in the art can realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment can be combined with the features, components, and/or steps described with respect to other embodiments of the present disclosure. For the sake of brevity, however, the numerous iterations of these combinations will not be described separately.

The present disclosure relates generally to OCT probes, OCT systems, and methods that scan tissue to obtain an OCT image. The probe can include a cannula configured to invasively penetrate patient tissue, such as the globe of an eye. The cannula can house a lens and an optical fiber. The fiber directs light through the lens and captures reflected light that passes back through the lens. To obtain a scan of an area or a line of tissue, rather than merely a point, the fiber can be moved within the cannula relative to the lens to cause the light emerging from the lens to scan across the desired pattern. Because the cannula that penetrates the patient tissue is desirably small in cross-section, moving the fiber within the cannula is difficult. The small amount of available space within the probe limits the types of actuators that can be utilized to impart movement to the fiber. In some instances it is desirable to manufacture the probe, or at least a portion thereof, as a disposable component, which requires product designs having cost-effective manufacturing techniques.

Exemplary aspects described herein utilize a technique of moving all or some portion of the fiber within the probe using an actuator system positioned within the probe that overcomes one or more of the problems or limitations of previous approaches. In some aspects described herein, the actuator system can include a mechanical structure and an electrically energizable member configured to selectively impart motion to the mechanical structure upon the electrically energizable member being electrically energized. The electrical energizable member can include an actuator. The mechanical structure can include a lever arm. The actuator can be connected to the first member of a lever arm. A second member of the lever arm can be connected to a fiber or fiber assembly that is desired to be actuated. The first member of the lever arm can be shorter than the second member of the lever arm. The fiber or fiber assembly can include a stiffening member through which the fiber or fiber assembly passes. The stiffening member can provide rigidity to the fiber when such rigidity is desired. The shape of the members of the lever arm can be straight or angled with respect to one another to accommodate space requirements or to change the direction of the actuation. The lever arm can pivot as it is actuated, causing the attached fiber or fiber assembly to be actuated by a multiplication of the ratio of the lengths of the lever arm members. The lever arm can have a pin or other similar component about which it pivots, or the lever arm can pivot by a flexure bearing (e.g., a living hinge, etc.). The lever arm can be configured in a symmetrical manner to produce a motion in the fiber that is linear. The symmetrical configuration can be achieved by arranging two lever arms in a mirror-like manner. Both short members of the lever arms can directly or indirectly contact the actuator, and the long members of the lever arm can contact the fiber or fiber assembly. Ends of both respective lever arm members can be directly or indirectly connected by flexible connective members. The lever arms can pivot by a pin pivot and/or a flexure bearing.

In some aspects described herein, the principle of a class 1 lever (mechanical advantage can be greater than 1) can be implemented to achieve a multiplication of stroke for actuation of a fiber or fiber assembly in conjunction with a scanning OCT endoscope. This can overcome the need to directly actuate the fiber with an actuator with a large stroke or rely on long extensions of the actuator, which is effectively a class 3 lever (mechanical advantage is less than one). In some aspects described herein, the lever arm members can be arranged/positioned in a manner that can allow advantageous arrangements of the actuator with respect to the fiber or fiber assembly in the probe housing.

In some aspects described herein, the mechanical structure of the actuator system can include a flexure mechanism and actuator. The flexure mechanism can be attached to the actuator at one location and to a fiber or fiber assembly at a second location. The flexure mechanism can be shaped as a rhombus, including four members connected by flexible joints at each vertex. The rhombus can be elongated in one axis and foreshortened in the other axis as measured from one vertex to the other opposing vertex. The actuator can be attached to one of the vertices in the elongated axis. The opposing vertex can be fixed. The fiber or fiber assembly can be attached to one of the vertices along the foreshortened axis. The opposing vertex can be fixed. When the actuator moves, the flexure mechanism can accommodate by changing shape. With one each of the vertices on the elongated and foreshortened axis fixed, the vertex with the fiber or fiber assembly attached can respond by moving outward, providing both a multiplication of the actuator stroke and a change of direction of the actuation.

In some aspects described herein, a flexure mechanism can be implemented to achieve a magnification of stroke for actuation of a fiber or fiber assembly in conjunction with a scanning OCT endoscope. This can overcome the need to directly actuate the fiber with an actuator with a large stroke. In some aspects described herein, the flexure mechanism can be arranged/positioned in a manner that can allow advantageous arrangements of the actuator with respect to the fiber or fiber assembly in the probe housing.

In some aspects, the actuator system can be configured to impart amplified motion to a distal section of the optical fiber. For example, the optical fiber can be positioned within the probe so that a distal end of the optical fiber extends past a distal end of the electrically energizable member and/or the mechanical structure of the actuator system such that motion imparted to the distal section of the optical fiber is amplified relative to movement of a portion of the optical fiber proximate to and/or longitudinally coextensive with the electrically energizable member and/or the mechanical structure.

In some aspects described herein, actuator systems that are inexpensive and have sufficient stroke to move the fiber or fiber assembly to achieve the OCT scan are provided. In some aspects, actuator systems that can both be compact enough so that they are packaged in an envelope defined by the imaging probe and provide motion in a direction that is needed to move the fiber or fiber assembly are shown and described. In some aspects, actuator systems that provide a multiplication of stroke from the actuator and a mechanism to change the direction of actuation are provided.

FIG. 1 is a diagrammatic schematic view of an arrangement illustrating aspects of the present disclosure. In particular, an eye 100 under treatment is shown. The eye 100 includes sclera 102, a cornea 104, an anterior chamber 106, and a posterior chamber 108. A capsular bag 110 is illustrated in the posterior chamber 108. The eye 100 further includes a retina 112.

An exemplary imaging system 120 is also illustrated in FIG. 1. As discussed in greater detail below, imaging system 120 is configured to image portions of the eye 100, such as the retina 112. The imaging system 120 can include a light source 122, an optical coherence tomography (OCT) system 124, a controller 126, a user interface 128, and a probe 130. The light source 122 is configured to provide imaging light that will be directed onto the target biological tissue by the probe 130. The light source 122 can be made up of super-luminescent diodes, ultra-short pulsed lasers, or supercontinuum lasers that provide relatively long wavelength light, such as between 700 nm and 1400 nm, between 700 nm and 900 nm, between 900 nm and 1200 nm, between 1000 nm and 1100 nm, between 1250 nm and 1450 nm, or between 1400 nm and 1600 nm. Imaging light reflected from the target biological tissue and captured by the probe 130 is utilized to generate images of the target biological tissue.

The OCT system 124 is configured to split the imaging light received from the light source 122 into the imaging beam that is directed onto the target biological tissue by the probe 130 and a reference beam that can be directed onto a reference mirror. The OCT system 124 can be a spectral domain or a time domain system. The OCT system 124 is further configured to receive the imaging light reflected from the target biological tissue and captured by the probe 130. The interference pattern between the reflected imaging light and the reference beam is utilized to generate images of the target biological tissue. Accordingly, the OCT system 124 can include a detector configured to detect the interference pattern. The detector can include Charge-Coupled Detectors (CCDs), pixels, or an array of any other type of sensor(s) that generate an electric signal based on detected light. Further, the detector can include a two-dimensional sensor array and a detector camera.

The controller 126 can include a processor and memory, which may include one or more executable programs for controlling aspects of the light source 122, the user interface 128, and/or the probe 130, and for executing and performing functions and processes to carry out an OCT imaging procedure. For example, the controller 126 is configured to control an actuation system of probe 130 configured to scan the imaging beam across the target biological tissue in some implementations.

One or more of the light source 122, the OCT system 124, the controller 126, and the user interface 128 can be implemented in separate housings communicatively coupled to one another or within a common console or housing. For example, in some implementations the light source 122, the OCT system 124, and the controller are positioned within a console that is communicatively coupled to the user interface 128. The user interface 128 can be carried on or form part of the console. Further, the user interface 128, or at least part(s) thereof, can be separate from the console. The user interface 128 can include a display configured to present images to a user or a patient, and display tissue scanned by the probe 130 during an OCT imaging procedure. The user interface 128 can also include input devices or systems, including by way of non-limiting example, a keyboard, a mouse, a joystick, a touchscreen, dials, and buttons, among other input devices.

The probe 130 is in optical communication with OCT system 124. In that regard, the probe 130 is configured to present light from the light source 122 that passes through OCT system 124 onto the target biological tissue for the purpose of imaging the tissue. Further, the probe can be in electrical communication with the controller 126. In that regard, the controller 126 can control an actuation system of the probe 130 via electrical signals sent to the probe 130 in order to cause the actuation system to scan the imaging beam across the target biological tissue. A cable 132 can connect the probe 130 to the OCT system 124 and/or the controller 126. In that regard, cable 132 can include optical fiber(s), electrical conductor(s), insulator(s), shield(s), and/or other features configured to facilitate optical and/or electrical communication between the probe 130 and the OCT system 124 and/or the controller 126. Further, it is understood that cable 132 can include multiple, separate cables. For example, in some instances an optical cable connects the probe 130 to OCT system 124 and a separate electrical cable connects the probe 130 to controller 126.

The imaging system 120 can include a connector that is configured to facilitate removable coupling of the probe 130 and/or the cable 132 with the OCT system 124 and/or the controller 126. The connector is configured to facilitate mechanical, optical, and/or electrical coupling of the probe 130 and/or the cable 132 with the OCT system 124 and/or the controller 126. For example, an optical fiber 138 extending along the length of the probe 130 is optically coupled to the OCT system 124 via the coupling of the connector with the OCT system 124. The optical fiber 138 can be a single fiber or a fiber bundle. In some embodiments, the connector is configured to threadingly engage with the OCT system 124 and/or the controller 126. However, it is understood that any type of selective engagement feature(s) or connectors can be utilized, including without limitation press fit, luer lock, threads, and combinations thereof, among other connection types. In some aspects, connector is located proximate to the OCT system 124 and/or the controller 126. The selective engagement of the connector at the OCT system 124 and/or the controller 126 allows the entire probe 130 to be a disposable component configured for use in a single procedure.

The probe 130 is sized and shaped to be handled by a surgeon and to protrude into a body of the patient. The probe 130 includes a housing 140 having a proximal portion 142 and a distal portion 144. The proximal portion 142 of the housing 140 can be sized and shaped for handheld grasping by a user. For example, the proximal portion 142 of the housing 140 can define a handle 146. The handle 146 can be sized and shaped for grasping by a single hand of the user. Further, the handle 146 can include a textured surface 148 (e.g., roughened, knurled, projections/recesses, tapers, other surface features, and/or combinations thereof) to enhance the user's grip on the handle 146. In use, the user controls the position of the distal portion 144 of the housing 140 by maneuvering the handle 146 such that the imaging light beam is directed towards the target biological tissue.

The distal portion 144 of the probe 130 can be sized and shaped for insertion into the eye 100 to be treated. In the illustrated embodiment of FIG. 1, the distal portion 144 of the probe 130 includes a cannula 150. The cannula 150 can be sized and shaped for insertion through the sclera 102 of the eye 100 to facilitate imaging of the retina 112. The cannula 150 can be integrally formed with the handle 146 as part of the housing 140. Alternatively, the cannula 150 and the handle 146 can be separate components fixedly secured to one another to form the housing 140. An optical element 152, such as a lens, can be secured within the distal end of the cannula 150. The optical element 152 is configured to focus the imaging light onto the target biological tissue, such as the retina 112. The optical element 152 can be, e.g., a gradient index (GRIN) lens, any other suitable lens, any suitable optical component(s), or a combination thereof. Depending upon the embodiment, the gradient index can be spherical, axial, or radial. The optical element 152 can also be a spherical lens. Other lens shapes can be used.

As will be discussed in greater detail below, the optical fiber 138 is moved with respect to the optical element 152 by an actuator system disposed within the probe 130 to cause the imaging beam—as focused by the optical element 152—to scan across a portion of the target biological tissue. FIGS. 2 and 5-10 described below illustrate various exemplary embodiments of actuator systems in accordance with the present disclosure. In that regard, it is understood that the actuator systems of the present disclosure can be positioned within the handle 146, within the cannula 150, and/or combinations thereof to move the optical fiber 138 across a desired scan pattern.

The distance of the focal point of the imaging beam from the distal end of the probe 130 can be determined by the optical element 152, a gap distance between the distal tip of the optical fiber 138 and a proximal face of the optical element 152, a numerical aperture of the optical fiber 138, and/or the wavelength of light of the imaging beam. For example, in some instances the focal power of the optical element 152 and/or the gap distance is selected to have a focus depth corresponding to likely distance of the distal end of the probe 130 from the target biological tissue during use. In some implementations of the probe 130 for retinal imaging, the focal point of the imaging beam can be between 1 mm and 20 mm, between 5 mm and 10 mm, between 7 mm and 8 mm, or approximately 7.5 mm beyond the distal end of the probe 130.

FIG. 2 is a stylized illustration of a cross-sectional side view of an imaging probe 190 in accordance with an aspect of the present disclosure. As shown, the optical fiber 138 extends along the length of the probe 190 through the handle 146 and the cannula 150. In the illustrated embodiment, an actuator system 192 is positioned within the handle 146. The optical fiber 138 can be fixed on a proximal portion of the probe 190. The actuator system 192 is configured to impart motion to the optical fiber 138 such that a distal end 180 of the optical fiber 138 moves with respect to the cannula 150 and optical element 152 that is fixedly secured to the cannula. More specifically, the distal end 180 of the optical fiber 138 can be moved with respect to the optical element 152 to scan the imaging beam across a desired pattern with respect to the target biological tissue.

The optical element 152 is configured to focus the imaging beam received from the optical fiber 138 onto the target biological tissue. In that regard, the optical element 152 includes a proximal face 182 and a distal face 184. The imaging beam enters the optical element 152 through proximal face 182 and leaves the optical element 152 through distal face 184. As shown, the proximal face 182 of the optical element 152 can extend at an oblique angle with respect to the longitudinal axis of the cannula 150. By having the proximal face 182 oriented at an oblique angle, the amount of reflection resulting from the imaging beam entering the optical element 152 can be reduced. In other embodiments, the proximal face 182 extends perpendicular to the longitudinal axis of the cannula 150.

The distal end 180 the optical fiber 138 can be spaced from the proximal face 182 of the optical element 152. In that regard, the spacing between the distal end 180 of the optical fiber 138 and the proximal face 182 of the optical element 152 can be selected to achieve a desired optical performance (e.g., focal distance, focus size, etc.). The spacing between the distal end 180 of the optical fiber 138 and the proximal face 182 of the optical element 152 can also be selected to allow a desired range of motion of the optical fiber 138 within the cannula 150 without physically contacting the optical element 152. The optical element 152 can be mechanically coupled to the distal end 180 of the optical fiber 138 so that the optical element 152 moves with the distal end 180 of the optical fiber 138.

The actuator system 192 is configured to impart motion to the optical fiber 138 such that the distal end 180 of the optical fiber 138 can be moved with respect to the optical element 152 to scan the imaging beam across a desired pattern with respect to the target biological tissue. The actuator system 192 can utilize a mechanical structure, such as a lever arm 196, and an electrically energizable member 194 to impart motion to an optical fiber positioned within an imaging probe. The actuator system 192 is configured to cause the lever arm 196 to move with respect to the housing in response to selectively, electrically energizing electrically energizable member 194. By utilizing a lever arm 196 to actuate the optical fiber 138, the mechanical advantage associated with the lever arm can be realized during actuation of the optical fiber 138.

In some embodiments, all or some portion of the optical fiber 138 within the probe 190 (e.g., the distal end 180) moves, for example, between 10 µm and 500 µm, between 50 µm and 500 µm, between 100 µm and 400 µm, or between 100 µm and 300 µm across the proximal face 182 of the optical element 152. The resulting optical scan is projected to the target biological tissue at a distance between, for example, 1 mm and 20 mm from the distal end of the cannula 150 (e.g., the focal point of the imaging beam, as described above). The linear extent of the imaging beam at the target biological tissue can be between 1 mm and 10 mm, between 1 mm and 8 mm, or between 1 mm and 5 mm. For example, there can be between approximately 50× and approximately 1000× multiplication of the distance the fiber moves across the proximal face 182 of the optical element 152 compared to the linear extent of the imaging beam at the target biological tissue.

The electrically energizable member 194 is shown to be cantilevered from a proximal portion of the handle 146. That is, a proximal portion 212 of the electrically energizable member 194 can be fixedly coupled to the housing defining handle 146, and a distal portion 214 of the electrically energizable member 194 can be movable with respect to the handle 146. The distal portion 214 can contact and apply a force to a proximal section 198 of the lever arm 196. The electrically energizable member 194 can be and/or include various components. For example, the electrically energizable member 194 can be a bi-morph piezoelectric actuator, linear actuator, solenoid actuator, etc.

The lever arm 196 can include the proximal section 198 and a distal section 200. The electrically energizable member 194 can be in contact with and/or apply a force to the proximal section 198 when electrically energizable member 194 is in an activated state (as electrically energizable member 194 may be in, e.g., FIG. 2). In an inactivated state, electrically energizable member 194 does not apply a force to lever arm 196. The electrically energizable member 194 can be in contact with or separated from lever arm 196 when electrically energizable member 194 is in an inactivated state. For example, the distal portion 214 can be disposed parallel to a longitudinal axis of probe 190 and separated from lever arm 196 when electrically energizable member 194 is in an inactivated state. In some embodiments, the distal portion 214 of electrically energizable member 194 is movable with respect to handle 146 and at least partially independent of movement of lever arm 196. In some embodiments, the distal portion 214 of electrically energizable member 194 and the proximal section 198 of lever arm 196 are in contact with one another and mechanically coupled using a suitable adhesive (e.g., glue, epoxy, etc.), mechanical connection, and/or combinations thereof.

The distal section 200 of the lever arm 196 can be in contact with and/or coupled to the optical fiber 138. Contact and/or coupling between the distal section 200 and the optical fiber 138 can be direct, indirect, or some combination thereof. For example, distal section 200 of the lever arm 196 can contact the optical fiber 138 directly or distal section 200 can contact a stiffening member 216 that is positioned adjacent to the optical fiber 138. In some embodiments, the distal section 198 of lever arm 196 and the optical fiber 138 are mechanically coupled by using a suitable adhesive (e.g., glue, epoxy, etc.), mechanical connection, and/or combinations thereof. In some embodiments, the distal section 198 is movable with respect to handle 146 and at least partially independent of movement of the optical fiber 138.

Electrically energizable member 194 can be configured to selectively impart motion to the lever arm 196 upon the electrically energizable member 194 being electrically energized. The electrically energizable member 194 can contact and/or apply a force to the proximal section 198 of the lever arm 196 in a direction 208 that causes the lever arm 196 to rotate about a pivot point 202. The pivot point 202 can be a location at which the lever arm 196 is referenced to, affixed, and/or mechanically coupled to handle 146. The pivot point 202 can include a pin, a flexure bearing, etc. The lever arm 196 can be pivotally affixed to the handle 146 by a pivot pin. When the lever arm 196 rotates about the pivot point 202, the distal section 200 of lever arm 196 can contact and/or apply a force to optical fiber 138 in a direction 210. As described in more detail in the discussion of FIGS. 3 and 4, contact with and/or the application of force by the distal section 200 of lever arm 196 on optical fiber 138 in the direction 210 causes movement of the distal end 180 of the optical fiber 138 in a direction 204. Lever arm 196 and/or electrically energizable member 194 are configured to be positioned in various parts of probe 190. In some embodiments, electrically energizable member 194 can apply a force to lever arm 196 in direction 210, and lever arm 196 can correspondingly apply a force to the optical fiber 138 in the direction 208. Thus, electrically energizable member 194 and lever arm 196 can apply force in various directions depending on their positions inside probe 190.

The application of force by the electrically energizable member 194 on lever arm 196 can be described as an actuation stroke. The resulting application of force on the optical fiber 138 by lever arm 196 can be described as a reaction stroke. Actuator system 192 allows the reaction stroke to experience the mechanical advantage associated with the lever arm 196 such that the reaction stroke is multiplied compared to the actuation stroke. In the discussion herein, the proximal section 198 of lever arm 196 can be variously referred to as the "short arm" and/or "first section" of lever arm 196, and the distal section 200 can be variously referred to as the "long arm" and/or "second section" of lever arm 196. The proximal section 198 can have a shorter length compared to distal section 200. The force acting on optical fiber 138 is equal to the force applied by the electrically energizable member 194 to the proximal section 198 multiplied by the ratio of the lengths of the proximal section 198 and the distal section 200. The lengths can be variously chosen such that a desired amount of force is imparted to the optical fiber 138. The desired amount of force can correspond to a desired amount of movement for the optical fiber 138. In other embodiments, the lengths can be variously chosen such that the lever arm 196 and other components of probe 190 properly fit in an interior of handle 146. Lever arm 196 and/or the electrically energizable member 194 can be entirely or partially disposed in a different portion of handle 146 (compared to the illustrated embodiment of FIG. 2) and/or in the cannula 150.

The probe 190 can include stiffening member 216 positioned adjacent to optical fiber 138 such that the distal section 200 of the lever arm 196 contacts the stiffening member 216 when electrically energizable member 196 is activated. When distal section 200 of the lever arm 196 contacts and/or applies force on stiffening member 216 and causes stiffening member 216 to move, optical fiber 138 moves correspondingly. Stiffening member 216 can be configured to distribute the force acting on optical fiber 138 across a greater distance compared to when the same force is applied directly to optical fiber 138 at a point or small range of contact between the optical fiber 138 and lever arm 196. Contact between optical fiber 138 and lever arm 196 at a point or small range can cause a central portion 218 of optical fiber 138 to bend or deflect in direction 210. In response to such bending and/or deflecting at the central portion 218 of optical fiber 138, the distal end 180 of the optical fiber 138 can be displaced in direction 206 such that optical fiber 138 is at least partially arcuately shaped. In some embodiments, such bending of the optical fiber 138 is desired for oscillation of the optical fiber 138. In other embodiments, such bending is undesired, and the stiffening member 216 can be provided to counteract it. Stiffening member 216 can be formed of a material that is more rigid than optical fiber 138 such that stiffening member 216 bends less when force is applied to it compared to when the same amount of force is applied directly to the optical fiber 138. Thus, stiffening member 216 can be configured to dampen the bending force acting on optical fiber 138 and lessen the amount of corresponding bending by the optical fiber 138. Stiffening member 216 can be provided when the bending force imparted by the lever arm 196 on optical fiber 138 is greater than desired.

When the stiffening member 216 is included in probe 190, it can extend longitudinally along at least a portion of optical fiber 138 and probe 190. The stiffening member 216 can be disposed entirely in cannula 150 or housing 146, or portions of stiffening member 216 can be partially disposed in both cannula 150 and housing 146. In some embodiments, stiffening member 216 can be described as a stiffening tube that is disposed annularly around optical fiber 138. For example, stiffening member 216 can extend around an entirety of the perimeter of optical fiber 138. In other embodiments, stiffening member 216 can be described as a stiffening plate disposed adjacent to at least a portion of the optical fiber 138. Such a stiffening member can be linear, curved, or some combination thereof. The stiffening member 216 can be secured to the optical fiber 138 and/or handle 146 using a suitable adhesive (e.g., glue, epoxy, etc.), mechanical connection, and/or combinations thereof. In the discussion herein, where a lever arm, a lever arm assembly, and/or a flexure mechanism is described as contacting an optical fiber, it is understood that this includes direct contact with the optical fiber 138, indirect contact (e.g., through stiffening member 216), and/or a combination thereof.

When stiffening member 216 is provided in handle 146, the stiffening member 216 can be bent in a biasing direction to provide a compliant restoration force for optical fiber 138, lever arm 136, and/or electrically energizable member 194 (e.g., toward a neutral position when the optical fiber 138 is coaxial with a longitudinal axis of cannula 152). For example, the stiffening member 216 could be bent in the direction 208 such that optical fiber 138 is biased towards the neutral position (e.g., in a direction opposite the direction 210 that optical fiber 138 is urged by lever arm 196 when electrically energizable member 194 is activated). The stiffening member 216 can be bent in addition to or in lieu of one or more restoring elements that are configured to return optical fiber 138, lever arm 136, and/or electrically energizable member 194 to a neutral position.

As shown, the optical fiber 138 is coupled to the lever arm 196 such that the distal end 180 of the optical fiber 138 extends distally beyond the distal section 200 of the lever arm 196. In this manner, the distal end 180 of the optical fiber 138 is cantilevered from the lever arm 196. As a result, the motion profile of the distal end 180 of the optical fiber 138 is amplified relative to the motion profile of the distal section 200 of the lever arm 196. In other words, the movement of the distal end 180 of the optical fiber 138 is greater than the corresponding movement of the distal section 200 of the lever arm 196. Movement of the distal section 200 of the lever arm 196 is caused when electrically energizable member 194 is energized, contacts, and/or applies force to proximal section 198, resulting in clockwise rotation of the lever arm 196 about pivot point 202 (as probe 130 is viewed from the perspective shown in FIG. 3). For example, when the distal section 200 of the lever arm 196 contacts and/or applies force to optical fiber 138 as indicated by arrow 210, the distal end 180 of the optical fiber will move as indicated by arrow 204 a greater distance in the same direction. When the distal section 200 of the lever arm 196 is moved away from optical fiber 138 (e.g., when electrically energizable member is no longer energized), the distal end 180 of the optical fiber 138 will move as indicated by arrow 206. In some embodiments, the weight of the optical fiber 138 and/or stiffening tube 216 alone causes movement of the optical fiber 138 in direction 206. In other embodiments, one or more restoring elements can be provided in probe 190 that directly and/or indirectly urges optical fiber 138 in direction 206. When moving in the direction 206, distal end 180 can move beyond a neutral position of optical fiber 138 (e.g., when optical fiber is coaxial with a longitudinal axis of cannula 152). The ratio of the movement of the distal end 180 of the optical fiber 138 to the movement of the distal section 200 of the lever arm 196 can be between 1.01:1.0 and 10.0:1.0, between 1.1:1.0 and 5.0:1.0, or between 1.5:1.0 and 2.0:1.0. Accordingly, the resultant movement of the distal end 180 of the optical fiber 138 can be more than 1%, 10%, 20%, 50%, 100%, 500%, or 1000% greater than the movement of the distal section 200 of the lever arm 196.

In some instances, the motion profile of the distal end 180 of the optical fiber simulates a lever arm action with a pivot point within the handle 146 of the probe 130. For example, the pivot point can be defined by point of contact between the lever arm 196 and optical fiber 138. In some instances, the optical fiber 138 can maintain a linear orientation during movement. In other instances, the optical fiber 138 bends during movement such that at least a portion of the optical fiber 138 has an arcuate shape. For example, in some instances the distal end 180 of optical fiber 138 bends relative to its proximal section that is fixed to handle 146 during movement caused by electrically activating the electrically energizable member 194.

Generally, the actuator system 192 is configured to move the electrically energizable member 194 from an inactivated state to one or more activated states. In an activated state, the electrically energizable member 194 applies a force to and causes rotation of lever arm 196, and lever arm 196 in turn applies a force to optical fiber 138. As a result, the actuator system 192 is configured to move optical fiber 138 (e.g., the distal end 180, the central portion 218, etc.) from a neutral position to one or more activated positions. In a neutral position, the optical fiber 138 can be positioned at any location within the lumen of the cannula 140. For example, all or some portion of the optical fiber 138 within the probe 190 can be coaxial with the longitudinal axis of the cannula 150 (as shown in, e.g., FIG. 2), proximate to and/or in contact with one wall of the cannula 150 (as shown in, e.g., FIGS. 3 and 4), etc. Similarly, in one or more activated positions, the optical fiber 138 can be coaxial with the longitudinal axis of the cannula 150 (as shown in, e.g., FIG. 2), proximate to and/or in contact with one wall of the cannula 150 (as shown in, e.g., FIGS. 3 and 4), etc.

For example, FIG. 2 illustrates an embodiment where the neutral position of the optical fiber 138 is coaxial with the longitudinal axis of the cannula 150. The actuator system 192 is configured to move the distal portion 214 of the electrically energizable member 194 and the distal section 200 of the lever arm 196 when electrically energizable member 194 is activated. In some embodiments, the distal end 180 of the optical fiber 138 can thereby move from the position coaxial with the longitudinal axis to an activated position in the direction 204 (as depicted in FIG. 3). When electrically energizable member 194 is no longer activated, the distal portion 214 of the electrically energizable member 194 and the distal section 200 of the lever arm 196 can return to their neutral position and/or cease applying force to lever arm 196 and optical fiber 138, respectively. Because optical fiber 138 is no longer being urged in the direction 210, the distal end 180 can move towards its neutral position in the direction 206. The weight of optical fiber 138 and/or the force applied by one or more restoring elements can cause movement of optical fiber 138 in direction 206. As depicted in FIG. 4, optical fiber 138 can, because of the momentum associated therewith, move past its neutral position in the direction 206. Optical fiber 138 can then move in the direction 204 and direction 206 before settling into the neutral position. In other embodiments, during a scanning process when optical fiber 138 is being oscillated, electrically energizable member 194 can be activated for a subsequent time (e.g., during a next frequency cycle) despite optical fiber 138 not being in the neutral position. For example, optical fiber 138 can be actuated after it moves past the neutral position in the direction 206 but before optical fiber 138 returns to the neutral position. In some embodiments, the optical fiber 138 maintains a linear profile during oscillation. In other embodiments, as described herein, the optical fiber 138 is at least partially arcuately shaped during oscillation.

In some embodiments, when the distal section 200 of lever arm 196 contacts, applies a force to, and/or urges the optical fiber 138 in direction 210, the distal end 180 of the optical fiber 138 can move in the direction 206. Such movement can occur, for example, when the central portion 218 of the optical fiber 138 bends or deflects in the direction 210. The distal end 180, in response to the bending or deflection of the central portion 218, can move in the direction 206 such that the optical fiber 138 is at least partially arcuately shaped. When the distal section 200 of lever arm 196 no longer applies a force to and/or urges optical fiber 138 in direction 210, optical fiber 138 can return towards its neutral position. The central portion 218 of the optical fiber 138 can move in direction 208, and the distal end 180 of the optical fiber 138 can move in direction 204. The optical fiber 138 can move past its neutral position because of the momentum associated therewith. When this occurs, the central portion 218 can bend or deflect in direction 208 and the distal end 180 can move in direction 204 such that the optical fiber 138 is at least partially arcuately shaped. In some embodiments, during a scanning process when optical fiber 138 is being oscillated, the optical fiber 138 periodically switches between having at least partial arcuate shapes that are mirror images of one another.

The electrically energizable member 194 can have two states: an inactivated state and an activated state. In an inactivated state, the electrically energizable member 194 is not energized, is not in contact with, does not apply a force, and/or does not urge the lever arm 196. For example, a bimorph piezoelectric actuator can extend parallel to optical fiber 138 in an inactivated state such that distal portion 214 is not in contact with lever arm 196. In some embodiments, such as when the distal portion 214 of the electrically energizable member 194 is coupled to the proximal section 196 of the lever arm 196, the electrically energizable member 194 is in contact with the lever 196 in an inactivated even though electrically energizable member 194 does not apply a force to and/or does not urge the lever arm 196. In an activated state, the electrically energizable member 194 is energized, is in contact with, does apply a force to, and/or does urge the lever arm 196. When energized, electrically energizable member 194 can bend such that at least a portion (e.g., distal portion 214) has an arcuate shape. For example, as shown in, e.g., FIG. 2, distal portion 214 bends, curves, or otherwise moves such that it contacts and/or applies force to the lever arm 196. Distal portion 214 can contact and/or apply force to the proximal section 198 of lever arm 196 in the direction 208. This can cause rotation of lever arm 196 about pivot point 202 in a counterclockwise direction (as probe 130 is viewed from the perspective shown in FIG. 2). Distal section 200 of lever arm 196 can slide or translate in a proximal direction from an initial point of contact with the optical fiber 138 when lever arm 196 rotates and distal section 200 applies a force to optical fiber 138. Rotation of lever arm 196 results in contact and/or the application of force by distal section 200 on optical fiber 138 in the direction 210. That is, a distal section 200 of the lever arm 196 experiences a multiplication of stroke and moves in the direction 210. The force can be applied to the lever arm 196 in a direction 208 (e.g., a first direction) that is opposite the direction (e.g., a second direction) that force is applied to optical fiber 138 (indicated by arrow 210). When electrically energizable member 194 is no longer being energized, the electrically energizable member 194 can return to the inactivated state. Thus, the distal portion 214 of electrically energizable member 194 no longer contacts and/or no longer applies a force to proximal section 198 of lever arm 196.

Because of the weight of lever arm 196 itself or the weight of the optical fiber 138 in addition thereto, lever arm 196 then rotates in a clockwise direction (as probe 130 is viewed from the perspective shown in FIG. 2), and distal section 200 no longer contacts and/or no longer applies a force to optical fiber 138.

Movement of the distal end 180 of the optical fiber 138 can be caused by selectively energizing electrically energizable member 194 such that the electrically energizable member 194 switches (e.g., in a manner that is periodic, oscillatory, etc.) between the inactivated and activated states. When the electrically energizable member 194 switches between the inactivated and activated states, force is either applied to optical fiber 138 by lever arm 196 in the direction 210 or not. This causes corresponding movement of distal end 180 of optical fiber 138 in directions indicated by arrows 204 (when electrically energizable member is energized) and 206 (when electrically energizable member is not energized).

By moving the optical fiber 138 to the activated position and then effectively releasing the optical fiber to move towards the neutral position, as illustrated in FIGS. 3 and 4, the optical fiber 138 can be oscillated and the imaging beam can be scanned across the target biological tissue, such as the retina. In some implementations, the actuator system 178 is configured to oscillate the distal end 180 of the optical fiber 138 within a frequency range between about 1 Hz and 100 Hz, between about 1 Hz and 50 Hz, between about 1 Hz and about 30 Hz, between about 5 Hz and 20 Hz, between about 10 Hz and 15 Hz, between about 1 Hz and 15 Hz, etc., although other frequency ranges, both larger and smaller, are contemplated. Electrically energizable member 194 can be in the activated state for one-half of a frequency cycle and in the inactivated state for one-half of the frequency cycle. The durations during which electrically energizable member 194 is in the activated and inactivated states may be greater than or less than one-half of the frequency cycle.

The positions of the distal end 180 of the optical fiber 138 depicted in FIGS. 3 and 4 can also be the neutral position for the actuator system 192. In that regard, the distal end 180 of the optical fiber 138 can begin in the position of FIG. 3 or FIG. 4 and then move to the position of FIG. 4 or FIG. 3, respectively, upon the electrically energizable member 194 being energized and lever arm 196 urging optical fiber 138 in direction 208 or 210.

When the electrically energizable member 194 is no longer energized and optical fiber 138 is no longer urged in the direction 208 or 210, optical fiber 138 moves towards its neutral position in the direction 204 or 206. As discussed below, in some implementations, the actuator system 192 can include one or more restoring elements to facilitate returning the electrically energizable member 194, the lever arm 196, and/or the optical fiber 138 to the starting, neutral position. The restoring element(s) can be mechanical and/or electromagnetic.

FIG. 5 is a stylized illustration of a cross-sectional side view of an imaging probe 220 in accordance with another aspect of the present disclosure. Probe 220 includes many features similar to those discussed above with respect to probe 130 and/or probe 190 that will not be repeated here for sake of brevity. Probe 220 includes an actuator system 222. The actuator system 222 is configured to impart motion to the optical fiber 138 such that the distal end 180 of the optical fiber 138 can be moved with respect to the optical element 152 to scan the imaging beam across a desired pattern with respect to the target biological tissue. The actuator system 222 can include a lever arm 196, electrically energizable member 194, and a restoring element 224. The restoring element 224 is configured to urge the lever arm 196 and/or electrically energizable member 194 and, thereby, the optical fiber 138 back to a starting position. The starting position can be a position similar to the positions shown in any of FIGS. 2-4.

The restoring element 214 can be a flexible restoring element. In the illustrated embodiment of FIG. 5, the restoring element 224 is a coil spring. In that regard, a lower portion of the coil spring is fixedly secured to the housing defining handle 146, while an upper portion of the coil spring is configured to interface with the proximal section 198 of lever arm 196. In particular, as the proximal section 198 of lever arm 196 is displaced when the electrically energizable member 194 is energized, the coil spring will be correspondingly compressed. When the electrically energizable member 194 is no longer energized, the potential energy resulting from compression of the flexible restoring element 224 will impart a restoring force on the lever arm 196 to cause it to return to its starting position. It is understood that restoring element 224 can be or include other structures (e.g., leaf spring, etc.)

FIG. 6 is a stylized illustration of a cross-sectional side view of an imaging probe 250 in accordance with another aspect of the present disclosure. Probe 250 includes many features similar to those discussed above with respect to probes 130, 190, and 220 that will not be repeated here for sake of brevity. Probe 250 includes an actuator system 252. In the illustrated embodiment of FIG. 6, the actuator system 252 includes a lever arm 256 and an electrically energizable member 264. Lever arm 256 includes many features similar to those discussed above with respect to lever arm 196. Electrically energizable member can be fixedly secured to handle 146 and mechanically coupled using a suitable adhesive (e.g., glue, epoxy, etc.), mechanical connection, and/or combinations thereof. Electrically energizable member 264 is shown to contact, apply a force to, and/or urge lever arm 256 in a direction perpendicular to the optical fiber 138 and/or a longitudinal axis of probe 250. The electrically energizable member 264 can be disposed in the handle 146 and provide the actuation motion to lever arm 256. For example, when electrically energizable member 264 is activated, shaft 254 can contact and/or apply a force to a proximal section 258 of the lever arm 256 in the direction 208. The lever arm 256 rotates in the counterclockwise direction (when probe 250 is viewed from the perspective shown in FIG. 6). Distal section 260 can be coupled to, contact, apply a force to, and/or urge optical fiber 138 in the direction 210.

In the illustrated embodiment of FIG. 6, electrically energizable member 264 is a solenoid actuator. It is understood that electrically energizable member 264 can be or include other structures (e.g., a bi-morph piezoelectric actuator, linear actuator, etc.) In the illustrated embodiment of FIG. 6, the proximal section 258 and distal section 260 of lever arm 256 are angled with respect to one another. The angle between proximal section 258 and distal section 260 can be between 0° and 180°, 30° and 150°, 45° and 135°, 60° and 120°, 75° and 105°, and 80° and 100°. Proximal section can angled towards electrically energizable member 264. It is understood that the proximal section 258 and distal section 260 can extend coplanar or parallel to one another (as shown in, e.g., FIGS. 2 and 5).

FIG. 7 is a stylized illustration of a cross-sectional side view of an imaging probe 280 in accordance with another aspect of the present disclosure. Probe 280 includes many features similar to those discussed above with respect to probes 130, 190, 220, and 250 that will not be repeated here for sake of brevity. Probe 280 includes an actuator system 282. Actuator system 282 is similar to actuator system 192 of probe 190 but includes a flexure bearing. The lever arm 284 can be movably affixed to the handle 146 by a flexure bearing. In the illustrated embodiment of FIG. 7, the flexure bearing is a living hinge. It is understood that any type of flexure bearing can be used. The flexure bearing can include a lower portion 290, a hinge 292, and an upper portion 294. The lower portion 290 of the flexure bearing is fixedly secured to the housing defining handle 146 while the upper portion of the flexure bearing is disposed between proximal section 286 and distal section 288 of lever arm 284 and/or forms a part of lever arm 284. Hinge 292 is configured to flex in the directions indicated by arrows 298 and 296. Hinge 292 can flex in direction 298 when electrically energizable member 194 applies a force on lever arm 284 in the direction 208. Hinge 292 can flex in direction 296 as lever arm 284 returns to a neutral position when electrically energizable member no longer applies a force on lever arm 284. Lever arm 284 may be integrally formed with the components of the flexure bearing, including the lower portion 290, the hinge 292, and the upper portion 294. Accordingly, lever arm 284 may rotate and/or move in the directions 298 and 296 as hinge flexes in directions 298 and 296, respectively. When electrically energizable member 194 is activated and contacts and/or applies a force to proximal section 286 of lever arm 284 in the direction 208, hinge 292 flexes in the direction 298. Hinge 292, upper portion 294, and lever arm 284, in solid lines, are shown as electrically energizable member 194 applies a force on lever arm 284. This correspondingly can cause distal section 288, in contact with optical fiber 138, to contact, apply a force to, and/or urge optical fiber 138 in the direction 210. Distal section 288 of lever arm 306 can slide or translate in a proximal direction from an initial point of contact with the optical fiber 138 when hinge 292 flexes and distal section 288 applies a force to optical fiber 138. When electrically energizable member 194 is no longer activated, hinge 292 flexes in the direction 296 towards a neutral position. Hinge 302, upper portion 304, and lever arm 306, in phantom lines, are shown in a neutral position, when electrically energizable member 194 does not apply a force on lever arm 196. Correspondingly, distal section 288 no longer contacts, applies a force to, and/or urges optical fiber 138.

Figure 9:
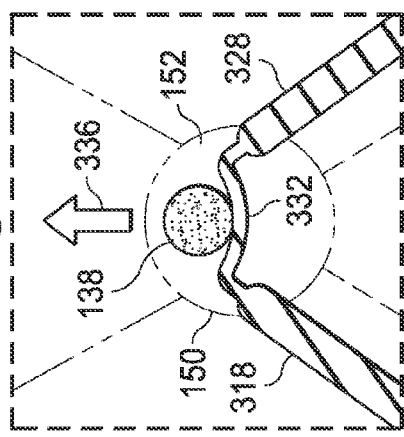
FIG. 9 is a stylized illustration of a cross-sectional back view of the imaging probe of FIG. 8 showing a flexible connecting member and an optical fiber of the imaging probe in accordance with an aspect of the present disclosure.

FIGS. 8 and 9 are described in the discussion below. FIG. 8 is a stylized illustration of a cross-sectional back view of an imaging probe 310 in accordance with another aspect of the present disclosure. FIG. 9 is a stylized illustration of a cross-sectional back view of the imaging probe of FIG. 8 showing a flexible connecting member and an optical fiber of the imaging probe in accordance with an aspect of the present disclosure. Probe 310 includes many features similar to those discussed above with respect to probes 130, 190, 220, 250, and 280 that will not be repeated here for sake of brevity. Probe 310 includes an actuator system 338. Actuator system 338 includes an electrically energizable member 313 and a lever arm assembly including lever arms 312 and 314 configured in a symmetrical manner. Lever arm 312 includes a first section 316, a second section 318, and a pivot point 320. Lever arm 314 includes a first section 326, a second section 328, and a pivot point 330. Lever arms 312 and 314 include many features similar to those discussed above with respect to lever arms 196 and 256. For example, first sections 316 and 326 are angled with respect to second sections 318 and 328, respectively. First section 316 and first section 326 can be mechanically coupled to one another via connecting section 322 and flexible connecting members 324. Second section 318 and second section 328 can be mechanically coupled via flexible connecting member 332. Optical fiber 138 can be received in a curvature of flexible connecting member 332. Thus, flexible connecting member 332 can be coupled to, contact, apply a force to, and/or urge optical fiber 138 in the direction 336. The configuration shown in FIG. 8 may be a neutral position of the lever arm assembly and/or the optical fiber 138.

Figure 10:
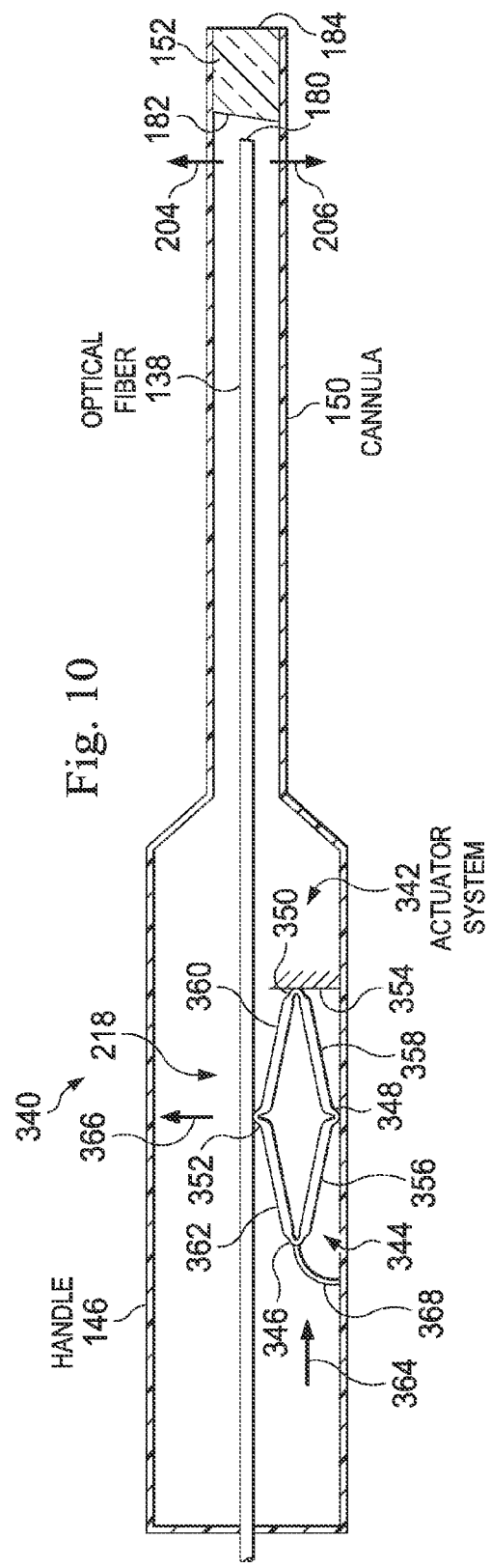
FIG. 10 is a stylized illustration of a cross-sectional side view of an imaging probe in accordance with another aspect of the present disclosure.

The lever arm assembly can be actuated by electrically energizable member 313. Electrically energizable member 313 can share features similar to those discussed above with respect to electrically energizable members 194 and 264. When activated, electrically energizable member 313 can contact and/or apply a force to connecting section 322 in the direction 334. Because lever arms 312 and 314 can be rigid and mechanically coupled to connecting section 322, lever arms 312 and 314 can rotate as result of the actuation. Lever arm 312 can rotate about pivot point 320 in a counterclockwise direction and lever arm 314 can rotate about rotate about pivot point 330 in a clockwise direction (when probe 310 is viewed in the perspective shown in FIG. 8). Rotation of lever arm 312 and 314 as described can cause flexible connecting member 332 to contact, apply a force to, and urge optical fiber 138 in the direction 336. As shown in the illustrated embodiment of FIG. 9, flexible connecting member 332 flattens as lever arms 312 and 314 rotate upon actuation by the electrically energizable member 313. The side of flexible connecting member 332 coupled to second section 318 of lever arm 312 is pulled to the left as lever arm 312 rotates in a counterclockwise direction. The side of flexible connecting member 332 coupled to second section 328 of lever arm 314 is pulled to the right as lever arm 314 rotates in a clockwise direction. Opposing forces on the left and right side of the flexible connecting member 332 cause it have less curvature. As flexible connecting member 332 flattens, the surface of flexible connecting member 332 in contact with the optical fiber 138 urges the optical fiber 138 in direction 336. That is, less surface area of the flexible connecting member 332 in contact with the optical fiber 138. This can cause optical fiber 138 (e.g., a distal end thereof) to be displaced with respect to optical element 152 in a distal portion of cannula 150. For example, as shown in FIGS. 9 and 10, optical fiber 138 can be displaced in direction 336 as a result of urging by flexible connecting member 332 compared to the relative positioning of optical element 152 and optical fiber 138 in the neutral position. The configuration shown in FIG. 9 can be an activated position of the lever arm assembly and/or the optical fiber 138.

When it returns to an inactivated state, the electrically energizable member 313 no longer applies a force to connecting section 322. The weight of the optical fiber 138 and/or of one or more components of the lever arm assembly can cause the lever arms 312 and 314 to rotate to a neutral position. As lever arm 312 rotates in a clockwise direction and lever arm 314 rotates in a counterclockwise direction, flexible connecting member 332 can bend such that a greater surface area of flexible connecting member 332 is in contact with the optical fiber 138 (e.g., as shown in FIG. 8). This can cause optical fiber 138 (e.g., a distal end thereof) to be displaced with respect to lens 152 in a distal portion of cannula 150 (in a direction opposite the direction that optical fiber 138 is displaced when electrically energizable member 313 is in an activated state). For example, as shown in FIGS. 10 and 9, optical fiber 138 can be displaced in a direction opposite direction 336 compared to the relative positioning of optical element 152 and optical fiber 138 in an activated position.

By oscillating the activation of the electrically energizable member, motion of optical fiber 138 in a similar manner as described with respect to FIGS. 3 and 4 can be achieved. In the illustrated embodiment of FIG. 8, the direction that the lever arm assembly is actuated (indicated by arrow 334) by the electrically energizable member 313 is the same as or parallel to the direction that the optical fiber 138 is actuated by the actuation system 338 (indicated by arrow 336).

The symmetrical lever arm assembly can produce motion of the optical fiber 138 that is linear (e.g., in direction 336) when such linear motion is desired. This is because any components of the force acting on the optical fiber 138 that are non-linear are generally caused by both lever arms 312 and 314. Because lever arms 312 and 314 are disposed on opposite sides of the optical fiber 138, the non-linear forces generally act in opposite direction and are generally canceled out. The linear component of the force remains and can impart linear motion to the optical fiber 138. In other embodiments, two-dimensional motion of the optical fiber 138 is desired, and the imaging probes described herein are configured to provide such motion.

The symmetrical lever arm assembly can also actuate the optical fiber 138 without having one or more components of the actuator system slide or translate longitudinally along the optical fiber 138. For example, in FIGS. 2, 5, and 6, distal section 200 of lever arm 196 can slide or translate along optical fiber 138 in a proximal direction starting from a point of initial contact with the optical fiber 138 as lever arm 196 applies a force to optical fiber 138. Such sliding or translating can be desirable in some embodiments. In other embodiments, sliding or translating is not desired. The symmetrical lever arm assembly (e.g., flexible connecting member 332) can apply a linear force in the direction 336 without sliding or translating along optical fiber 138 because the symmetrical lever arm assembly is positioned orthogonally to optical fiber 138. Thus, movement by the symmetrical lever arm assembly can occur and remain in a plane orthogonal to the optical fiber 138.

FIG. 10 is a stylized illustration of a cross-sectional side view of an imaging probe 340 in accordance with another aspect of the present disclosure. Probe 340 includes many features similar to those discussed above with respect to probes 130, 190, 220, 250, 280, and 310 that will not be repeated here for sake of brevity. Probe 340 includes an actuator system 342. The actuator system 342 includes a flexure mechanism 344, an electrically energizable member 368, and a fixing member 354. The flexure mechanism 344 can be variously shaped, including as a polygon, an ellipse, or a combination thereof. For example, the shape of flexure mechanism 344 can be described as a rhombus, a rhomboid, and/or a parallelogram. The flexure mechanism 344 has sides 356, 358, 360, and 362, and vertices 346, 348, 350, and 352. In some embodiments, sides 356, 358, 360, and 362 can have equal length. In some embodiments, two opposing sides have a first length and two opposing sides have second length. Vertices 346, 348, 350, and 352 can be or include one or more flexible connecting members that mechanically couple sides 356, 358, 360, and 362.

Electrically energizable member 368 can be positioned in handle 146 such that it contacts and/or applies a force to a vertex of the flexure mechanism 344 in the direction 364. In the illustrated embodiment of FIG. 10, electrically energizable member 368 is configured to contact vertex 346. Vertex 352 can be coupled to, contact, apply a force to, and/or urge the optical fiber 138 in the direction 366. The application of force by the electrically energizable member 368 on the flexure mechanism 344 can be described as the actuation stroke. The application of force by the flexure mechanism 344 on the optical fiber 138 can be described as the reaction stroke. Actuator system 342 enables the reaction stroke to experience the mechanical advantage associated with the flexure mechanism 344 such that the reaction stroke is multiplied compared to the actuation stroke. Actuation of the optical fiber 138 (the reaction stroke) experiences a multiplication of the actuation stroke by a function of the length of one or more sides 356, 358, 360, and 362.

The flexure mechanism 344 can be elongated in one axis and foreshortened in the other axis as measured from one vertex to the opposing vertex (e.g., from vertex 346 to vertex 350 or from vertex 352 to vertex 348). The axis defined from vertex 346 to vertex 350 can be the elongated axis, and the electrically energizable member can be configured to contact and/or apply a force to vertex 346 of the elongated axis. The opposing vertex 350 can be fixed to a fixing member 354. Fixing member 354 can be any structural component that prevents the longitudinal displacement of vertex 350 beyond a location defined by fixing member 354. Fixing member 354 may be fixedly secured relative to the handle 146. Because vertex 350 is fixed to fixing member 354, vertex 350 is also secured relative to the handle 146. By fixing vertex 350 to fixing member 354, the reaction stroke may be increased because the force acting on vertex 346 is carried through sides 356, 358, 360, 362 to the optical fiber 138. The axis defined from vertex 348 to 352 can be the foreshortened axis, and the flexure mechanism 344, coupled to optical fiber 138, can be configured to contact and/or apply a force to the optical fiber 138 at the vertex 352 of the foreshortened axis. The opposing vertex 348 can be fixed to the housing defining handle 146.

When acted upon by the electrically energizable member 368, the flexure mechanism 344 can accommodate by changing shape. With one of each of the vertices on the elongated and foreshortened axis fixed, the vertex 352 can respond by moving outward in the direction 366. Such movement of vertex 352 applies a force to optical fiber 138 in direction 366. Vertex 352 may slide or translate longitudinally along the optical fiber 138 in a distal direction from a point of initial contact with the optical fiber 138. In some embodiments, sides 356, 358, 360, 362 can include a connecting section and one or more flexible connecting members (e.g., similar to connecting section 322 and flexible connecting members 324 in FIG. 8). In such embodiments, the connecting section can be fixed to handle 146, fixing member 250, have a force applied thereto by electrically energizable member 368, and/or apply a force to optical fiber 138. Actuator system 342 also provides a change of direction of actuation. That is, the direction that flexure mechanism 344 is actuated by electrically energizable member 368 (indicated by arrow 364) is perpendicular to the direction that the optical fiber 138 is actuated by flexure mechanism 344 (indicated by arrow 366).

The motion profiles discussed in the context of the actuator systems above generally focused on linear displacement of the distal end 180 of the optical fiber 138 within cannula, which can be utilized to produce a corresponding linear scan of the imaging beam across the target biological tissue. In other embodiments, the optical probe includes, e.g., two actuator systems oriented perpendicular to one another with corresponding electrically energizable members that can be selectively energized to scan the optical fiber 138 and the imaging beam across a two-dimensional scanning pattern. One of the actuator systems can be configured to impart motion to the optical fiber 138 along a first axis and the other of the actuator systems can be configured to impart motion to the optical fiber 138 along a second axis perpendicular to the first axis. The two-dimensional scanning pattern can include a spiral, a raster, a constant-radius asterisk, a multiple-radius asterisk, a multiply folded path, other two-dimensional scan patterns, other patterns, and/or combinations thereof.

Embodiments as described herein may provide an imaging probe having an actuator system that utilize a mechanical structure, such as a lever arm or a flexure mechanism, and an electrically energizable member, such as an actuator, to impart motion to an optical fiber positioned within an imaging probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic imaging probe, comprising:
   a handle;
   a cannula coupled to the handle;
   an optical fiber positioned at least partially within the handle and the cannula, the optical fiber configured to receive an imaging light from an imaging light source and guide the imaging light to an optical element positioned within a distal portion of the cannula; and
   an actuator system configured to impart motion to the optical fiber, the actuator system including a mechanical structure and an electrically energizable member configured to selectively impart motion to the mechanical structure upon the electrically energizable member being electrically energized.

2. The probe of claim 1, wherein:
the mechanical structure is a lever arm.

3. The probe of claim 2, wherein:
the actuator system is configured to impart amplified motion to a distal section of the optical fiber.

4. The probe of claim 3, wherein:
the optical fiber is coupled to the lever arm so that a distal end of the optical fiber extends past a distal end of the lever arm such that motion imparted to the distal end of the optical fiber is amplified relative to the movement of the lever arm.

5. The probe of claim 2, wherein:
at least a portion of lever arm is configured to move relative to the handle in response to the electrically energizable member being electrically energized.

6. The probe of claim 2, wherein:
the lever arm is pivotally affixed to the handle by a pivot pin.

7. The probe of claim 6, wherein:
the lever arm is movably affixed to the handle by a flexure bearing.

8. The probe of claim 2, wherein the lever arm comprises:
a first section configured to contact the electrically energizable member; and
a second section configured to contact with the optical fiber.

9. The probe of claim 2, wherein:
the actuator system further includes a restoring element configured to counteract the motion imparted to the optical fiber by the lever arm in response to the electrically energizable member being electrically energized.

10. The probe of claim 9, wherein:
the restoring element is a flexible restoring element.

11. The probe of claim 2, wherein:
the electrically energizable member is configured to impart motion to a first arm of the lever arm in a first direction; and
in response to the motion imparted to the first arm of the lever arm by the electrically energizable member, a second arm of the lever arm is moved in a second direction to impart motion to the optical fiber.

12. The probe of claim 11, wherein:
the second direction is opposite the first direction.

13. The probe of claim 11, wherein:
the second direction is perpendicular to the first direction.

14. The probe of claim 1, wherein
a proximal section of the electrically energizable member is fixedly secured to a proximal portion of the handle.

15. The probe of claim 1, wherein:
a proximal section of the optical fiber is fixedly secured to a proximal portion of the handle.

16. The probe of claim 1, wherein:
the optical element comprises a gradient index (GRIN) lens.

17. The probe of claim 1, wherein:
the optical element is mechanically coupled to a distal end of the optical fiber so that the optical element moves with the distal end of the optical fiber.

18. The probe of claim 1, wherein:
the actuation system is configured to impart motion to the optical fiber to scan the imaging light along a scanning pattern with a linear extent at a target biological tissue between 1 mm and 5 mm at a distance between 5 mm and 10 mm from a distal end of the cannula.

19. The probe of claim 1, further comprising:
a stiffening member disposed adjacent to the optical fiber.

20. The probe of claim 1, wherein:
the mechanical structure is a flexure mechanism.

21. The ophthalmic imaging system of claim 20, wherein the flexure mechanism includes a first vertex configured to be displaced by the electrically energizable member and a second vertex configured to impart motion to the optical fiber in response to displacement of the first vertex.

22. The ophthalmic imaging system of claim 21, wherein:
the flexure mechanism further includes a third vertex positioned opposite the first vertex and a fourth vertex positioned opposite the second vertex, the third vertex and fourth vertex are fixedly secured to the handle.

23. An ophthalmic imaging system, comprising:
an imaging light source configured to generate an imaging light;
an optical guide in optical communication with the imaging light source, the optical guide configured to receive the generated imaging light from the imaging light source; and
a probe in optical communication with the optical guide, the probe including
a handle;
a cannula coupled to the handle;
an optical fiber positioned at least partially within the handle and the cannula, the optical fiber configured to receive an imaging light from an imaging light source and guide the imaging light to an optical element positioned within a distal portion of the cannula; and
an actuator system configured to impart motion to the optical fiber, the actuator system including a mechanical structure and an electrically energizable member configured to selectively impart motion to the mechanical structure upon the electrically energizable member being electrically energized, wherein the mechanical structure includes at least one of a lever arm and a flexure mechanism.

24. The ophthalmic imaging system of claim 23, further comprising:
a controller in communication with the light source, the controller configured to control actuation of the imaging light source for an optical coherence tomography (OCT) imaging procedure.

25. The ophthalmic imaging system of claim 24, wherein:
the controller is further configured to process data obtained by the probe and output imaging data to a display in communication with the controller.

26. A method of ophthalmic imaging, comprising:
energizing an electrically energizable member positioned within a housing of ophthalmic probe to deflect a lever arm within the housing;
wherein deflection of the lever arm causes an optical fiber coupled to the lever arm to scan an imaging light passing through the optical fiber across an optical element positioned within a distal portion of the housing.

* * * * *